United States Patent
Washio et al.

(10) Patent No.: US 9,241,639 B2
(45) Date of Patent: Jan. 26, 2016

(54) SYSTEM FOR ESTIMATING MEMBRANE STRESS ON ARBITRARILY-SHAPED CURVILINEAR SURFACE BASED ON CURRENT CONFIGURATION DATA

(76) Inventors: Takumi Washio, Ibaraki (JP); Toshiaki Hisada, Tokyo (JP); Eiji Nunobiki, Shizuoka (JP); Jun-ichi Okada, Chiba (JP); Seiryo Sugiura, Tokyo (JP)

( * ) Notice: Subject to any disclaimer, the term of this patent is extended or adjusted under 35 U.S.C. 154(b) by 382 days.

(21) Appl. No.: 13/642,332

(22) PCT Filed: Apr. 20, 2010

(86) PCT No.: PCT/JP2010/057322
§ 371 (c)(1),
(2), (4) Date: Oct. 19, 2012

(87) PCT Pub. No.: WO2011/132320
PCT Pub. Date: Oct. 27, 2011

(65) Prior Publication Data
US 2013/0041639 A1 Feb. 14, 2013

(51) Int. Cl.
*G06F 17/50* (2006.01)
*A61B 5/021* (2006.01)
*A61B 5/02* (2006.01)
*A61B 5/055* (2006.01)
(Continued)

(52) U.S. Cl.
CPC ............. *A61B 5/021* (2013.01); *A61B 5/02014* (2013.01); *A61B 5/055* (2013.01); *A61B 6/03* (2013.01); *A61B 8/14* (2013.01); *G06F 17/5018* (2013.01)

(58) Field of Classification Search
CPC ...... A61B 5/021; A61B 5/02014; A61B 8/14; A61B 5/055; G06F 17/5018

USPC .............................................. 703/2
See application file for complete search history.

(56) References Cited

U.S. PATENT DOCUMENTS 6,876,956 B1 * 4/2005 Cirak et al. ................ 703/2
7,899,516 B2 * 3/2011 Chen et al. ................ 600/419
(Continued)

FOREIGN PATENT DOCUMENTS

JP 2009-529944 8/2009

OTHER PUBLICATIONS

International Search Report from International Application No. PCT/JP2010/057322 mailed Jun. 8, 2010.
(Continued)

*Primary Examiner* — Dwin M Craig
(74) *Attorney, Agent, or Firm* — Brundidge & Stanger, P.C.

(57) ABSTRACT

A stress estimating system includes a polygon data input unit of polygon data modeling a vascular wall, an interactive analysis condition setting unit for setting the tensile force acting on the vascular wall boundary, blood pressure and constraint estimated as proper on the boundary, a stress analysis unit for obtaining two-dimensional stress by solving a mechanical equilibrium equation with respect to the membrane stress on a curvilinear surface of the vascular wall under the condition given by the polygon data input unit and the interactive analysis condition setting unit, and an interactive visualization unit for displaying a distribution of a stress component designated by a system user. Without assuming any symmetry for the curvilinear configuration and stress distribution, a complicated stress distribution is estimated only out of the mechanical equilibrium equation with respect to membrane stress.

2 Claims, 11 Drawing Sheets

(51) Int. Cl.
  *A61B 6/03*  (2006.01)
  *A61B 8/14*  (2006.01)

(56) References Cited

U.S. PATENT DOCUMENTS

2003/0222871 A1* 12/2003 Brombolich .............. 345/427
2005/0281447 A1* 12/2005 Moreau-Gobard et al. .. 382/130
2010/0049451 A1   2/2010 Lu

OTHER PUBLICATIONS

Japan Mechanical Engineers Association, Biomechanical Engineering, first edition, Maruzen, 1997.
Davies, et al., Yearly Rupture or Dissection Rates for Thoracic Aortic Aneurysms: Simple Prediction Based on Size, Ann. Thorac. Surg. vol. 73, pp. 17-28, 2002.
Beller, et al., Role of Aortic Root Motion in the Pathogenesis of Aortaic Dissection, Circulation 109, pp. 763-769, 2004.
Nunobiki, et al., Studies on Pathogenesis of Aortic Dissection, Japan Mechanical Engineers Association 20$^{th}$—Mechanics Conference., pp. 141-142, 2007. w/partial English translation.
Elger, The Influence of Shape on the Stresses in Model Abdominal Aortic Aneurysms, J. Biomech. Eng. vol. 118:3, Aug. 1996, pp. 326-332.
Yamada, et al., A Study on the Method of Stress Analysis for Abdominal Aortic Aneurysm (Case of non-axisymmetric geometry), The Japan Society of Mechanical Engineers, pp. 49-50, 2005.
Office Action issued in corresponding Japanese Patent Application No. 2012-511502, dated Nov. 12, 2013, with partial English translation.
Search Report issued in corresponding European Patent Application No. 10850261.8, dated Aug. 8, 2014.
Kroon, M., et al. "Elastic properties of anisotropic vascular membranes examined by inverse analysis", Computer Methods in Applied Mechanics and Engineering, North-Holland, Amsterdam, NL, vol. 198, No. 45-46, Sep. 15, 2009, pp. 3622-3632.
DePutter, S., et al: "Patient-specific initial wall stress in abdominal aortic aneurysms with a backward incremental method", Journal of Biomechanics, vol. 40, No. 5, Jan. 1, 2007, pp. 1081-1090.
Nunobiki, et al., "Studies on Pathogenesis of Aortic Dissection", Japan Mechanical Engineers Association 20th—Mechanics Conference, pp. 141-142, 2007. w/partial English translation.

* cited by examiner

```
START
  ↓
INPUT OF BLOOD PRESSURE ─── 0501
  ↓
INPUT OF
FIXED CONDITION INFORMATION ─── 0502
  ↓
INPUT OF TENSILE FORCE ─── 0503
  ↓
INPUT OF CONSTRAINT PORTION
AND CONSTRAINT ─── 0504
  ↓
SEND ANALYSIS CONDITION
INFORMATION TO ANALYSIS UNIT ─── 0505
  ↓
END
```

0604 — PERPENDICULAR COMPONENT OF ARROW DIRECTION IS FIXED

0603 — APPLYING TENSILE FORCE IN ARROW DIRECTION

0602 — CONSIDER AS FIXED PORTION

SYSTEM FOR ESTIMATING MEMBRANE STRESS ON ARBITRARILY-SHAPED CURVILINEAR SURFACE BASED ON CURRENT CONFIGURATION DATA

TECHNICAL FIELD

In a medical diagnostic systems, this invention is concerned with a diagnostic technique for estimating stress distribution on the vascular wall and evaluating its rupture risk based on curvilinear surface shape of vascular wall surrounding the blood domain which is obtained from medical image by diagnostic equipment, such as MRI, CT, ultrasound echo image.

BACKGROUND

Aneurysm of aorta and dissection of the aorta are typical diseases of the thoracic aorta, and there is an influential theory that those diseases are caused by aortic wall stress. Especially in relation to aortic aneurysm, magnitude of generated stress and risk of rupture of the aneurysm are considered to be directly related with each other. Decision of whether or not to perform operation has been judged by measuring the diameter of the aneurysm and evaluating the generated stress in the aneurysm based on the Laplace's law (approximation of thin-walled cylindrical shells) (C.f. Non-patent Literature 1) in clinical practice. However, this diagnostic method using only a representative dimension for evaluating stress of a complex shaped aneurysm includes a problem of accuracy, and cases have been reported where rupture occurred at an aneurysm shape to which operation had not been performed under the decision of the above-mentioned diagnostic method (C.f. Non-Patent Literature 2). In this regard, a development of stress evaluation method with higher accuracy is required, and the finite element analysis of individual aortic wall stress analysis is considered as one of the effective means.

Stress analysis of aortic wall has been numerously tried by now. For example, a three-dimensional finite element stress analysis (C.f. Non-Patent Literature 3) reproducing the effect of blood pressure and tensile force caused by the heart assuming the aortic wall as a linear elastic body, and a non-linear finite element analysis (C.f. Non-Patent Literature 4) reproducing blood pressure and tensile force and by using various constitutive laws as material models for the wall of blood vessel of the aorta and by using the shape model generated from the multi sliced CT of human thoracic aorta, have been performed.

However, the foregoing analysis methods have the following problems generally when applied to the bio-mechanical analysis. (a) Since it is impossible for measuring the material property parameters of aorta of each individual in vivo, modification of the experimental data conducted in vitro using a typical specimen is needed before the use. (b) Since it is also impossible for obtaining the shape of aorta under a non-loaded condition from CT images, some analysis must be done to modify the shape which was obtained from a loaded condition or a kind of residual stress must be introduced.

Conventional stress analysis methods caused by the analysis complexity and uncertainty in accordance with above problems will hardly become a practical diagnostic tool in the scene of clinical practice. On the other hand, an alternative approach for evaluating stress of the aortic wall by avoiding above problems has been tried. For example, there is a method of calculating maximum stress value only from the internal pressure and curvilinear shape (C.f. Non-Patent Literature 5) by assuming that the flexural rigidity of the blood vessel wall can be ignored, and using an axisymmetric model as an approximation of abdominal aneurysm of aorta, and there is also another attempt (C.f. Non-Patent Literature 6) extending this calculation method to a quasi-axisymmetric curvilinear surface.

CITATION LIST

Non-patent Literature

[Non-Patent Literature 1] Japan Mechanical Engineers Association, Biomechanical Engineering, first edition, Maruzen, 1997
[Non-Patent Literature 2] Davis R. R., Goldstein L. J., Coady M. A., Title S. L., Rizzo J. A., Kopf G. S., Elfteriades J. A., Yearly rupture or discussion rates for thoracic aneurysms: simple prediction based on size, Ann. Thorac. Surg. 73, pp. 17-27, 2002.
[Non-Patent Literature 3] Beller C. J., Labrosse M. R., Thubrikar M. J., Robicsek F., Role of aortic root motion in the pathogenesis of aortic dissection, Circulation 109, pp. 763-769, 2004
[Non-Patent Literature 4] Eiji Nunobiki, Hiroshi Watanabe, Seiryo Sugiuea, Toshiaki Hisada, studies on pathogenesis of aortic dissection, Japan Mechanical Engineers Association 20 times calculation mechanics Conference proc., pp. 141-142, 2007.
[Non-Patent Literature 5] Elger D. F. Blackketer D. M., Budwig R. S., The Influence of Shape on the Stresses in Model Abdominal Aortic Aneurysms, J. Biomech. Eng. 118, 3, 326, 1996.
[Non-Patent Literature 6] Yamada Hiroshi, Yuichi Hasegawa, studies of stress analysis for abdominal aortic aneurysm (of non-axisymmetric aneurysm shape), Japan mechanical engineers meeting 16 times biotechnology frontier conference proc. Pp. 49-50, 2005.

SUMMARY OF INVENTION

Technical Problem

However, in the conventional method for estimating the stress in accordance with curvilinear surface and the blood pressure, it is impossible to deal with a curvilinear surface which is largely apart from axisymmetric shape such as real thoracic aorta, and also under the assumption of symmetry of the stress field substantially, it is not allowed to deal with asymmetrical boundary condition for the applied force on the boundary.

This invention is made considering the above problems and the main purpose of this invention is to realize a diagnostic system for estimating the stress distribution on a vascular wall accurately under a rational assumption with only a mechanical equilibrium equation even for a complicated curvilinear surface shape.

Solution to Problem

The stress estimating system in this invention consists of a polygon data input unit for the vascular wall, an interactive analysis condition setting unit for setting a assumed tensile force on the vascular wall boundary, blood pressure and the constraint assumed as appropriate at the boundary, consists of a stress analysis unit for obtaining a two-dimensional stress distribution by solving mechanical equilibrium equation for the membrane stress on the curvilinear surface representing vascular wall given by the polygon data together with input unit and the interactive analysis condition setting unit, and consists of an interactive visualization unit for displaying a distribution of stress component designated by a system user. This system is especially characterized by solving the above problem without assuming any symmetry for the curvilinear surface shape and stress distribution, and enabling the estimation of a complicated stress distribution only by a mechanical equilibrium equation with membrane stresses.

In the stress analysis unit, using an adjoint operator of the divergence operator for membrane stress tensor in the mechanical equilibrium equation, the membrane stresses are transferred to the two dimensional strains, with which the above equilibrium equation is replaced by the second order elliptic partial differential equation with respect to the pseudo-displacement vector field. The partial differential equation prepared in this way is discretized by the finite elements under the boundary condition given by the interactive analysis condition setting unit on the mesh given by the polygon data input unit, to obtain numerical solution of the pseudo-displacement vector field. And, by calculating the two dimensional strain from the numerical solution of the pseudo-displacement vector field calculated in above, stress distribution over the whole membrane is obtained.

Furthermore, since the partial differential equation solved in the stress analysis unit is a linear equation, we can completely separate the effects on the resultant the stress from the blood pressure and from the tensile force and constraint on the boundary. In the stress estimating system of this invention, the tensile force can be set to zero in the interactive analysis condition setting unit when an user want to estimate the effect only from the blood pressure, and the analysis condition is passed on to the stress analysis unit. By this procedure, influence to the stress only by the blood pressure can be estimated. Or, when an user want to estimate the effect on the stress from the tensile force only, then the blood pressure is set to zero at the interactive analysis condition setting unit, and the analysis condition is hand on to the stress analysis unit. By this way, the effect on the stress field from only the tensile force can be estimated.

Advantageous Effect of Invention

As mentioned in above, in the stress estimating system of this invention, with the boundary condition applied to an appropriate vascular wall boundary which is modeled by polygon data, the finite element analysis is performed, and thus, there is no need for assuming the membrane shape or axisymmetric nature of stress at all. Furthermore, it is sufficient to introduce the shape of vascular wall at a timing of interest, and it is unnecessary to know the shape under no-loaded condition. In addition, since only vascular shape and appropriate boundary condition are necessary for the mechanical equilibrium equation to be solved in the stress analysis unit, it is unnecessary to introduce the parameters of material property at all.

Also, even when the tensile force and constraints on the boundary are uncertain, in the stress estimating system of this invention, since analysis can completely separate the effects from these boundary conditions and from the blood pressure, it is also possible to estimate the effect on the stress field only from the blood pressure.

THE BEST EMBODIMENTS FOR CARRYING OUT THE INVENTION

[First Embodiment]

The stress estimating system of this invention estimates two-dimensional stress (plane stress assuming all the stresses concerned with thickness direction is zero) from polygon data expressing shape of vascular wall after deformation obtained by a medical image, blood pressure estimated from other medical equipment, and tensile force applied to the vascular wall estimated from the blood pressure.

Figure 1:
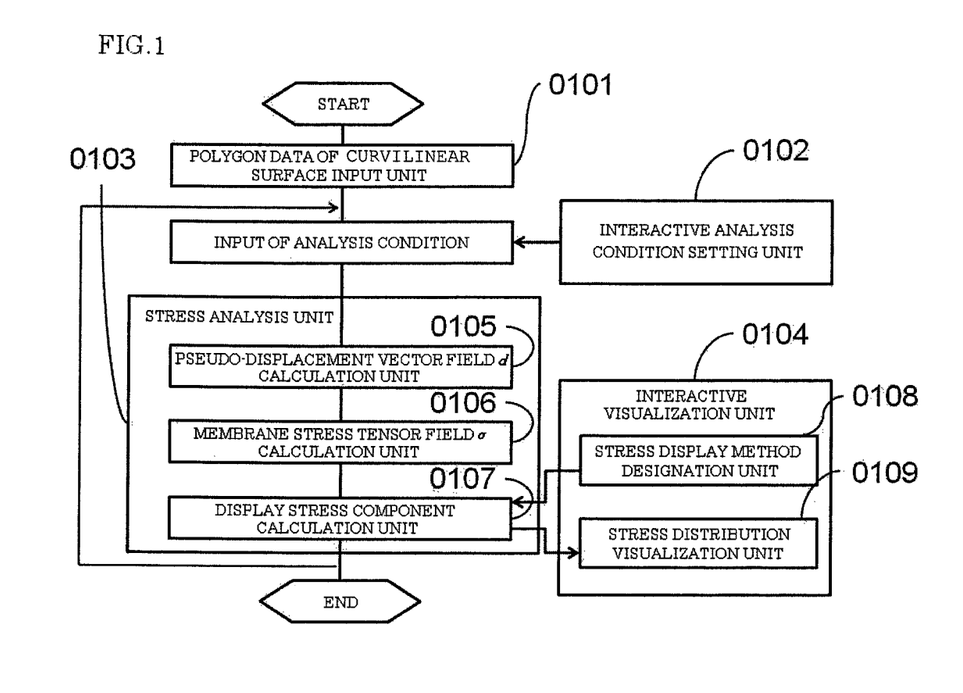
FIG. 1 A functional block diagram for showing a principal part of an embodiment of Stress estimating system in this invention.

FIG. 1 shows an embodiment of this invention, and a functional block indicating an essential part of the stress estimating system. From polygon data input unit of curvilinear surface of wall 0101, polygon data expressing curvilinear surface of wall is read. Through interactive analysis condition setting unit 0102, a user of this system designates blood pressure, constraint at boundary of curvilinear surface, and the tensile force acts at boundary. In stress analysis unit 0103, the two-dimensional stress on the curvilinear surface is calculated under the given analysis condition, stress component designated by designation unit of stress display method 0108 in the interactive visualization unit 0104 is obtained, and these results are returned to the interactive visualization unit 0104. In the interactive visualization unit 0104, the returned distribution of the stress component on the curvilinear surface is displayed to the system user by the stress distribution visualization unit 0109.

Figure 2:
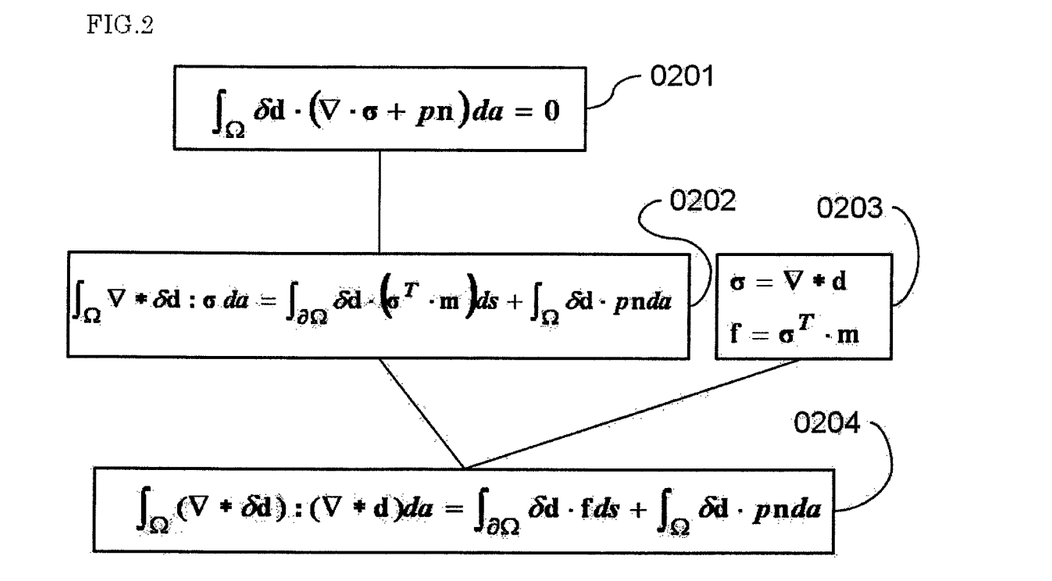
FIG. 2 A figure showing a principle utilized in an embodiment of stress estimating system.

FIG. 2 shows a principle utilized by the stress estimating system of this invention. Formula 0201 expresses a formula which should be satisfied by the membrane stress field on the curvilinear surface σ composed of membrane structure receiving internal pressure p. This membrane stress field is a two-dimensional stress to be estimated in here. By using Gauss's divergence theorem, formula 0201 is converted into formula 0202. In formula 0202, as being expressed by formula 0203 membrane stress field is expressed by two dimensional strain using the pseudo-displacement vector field d, and by replacing force $\sigma^T \cdot m$ at boundary with traction f given by interactive analysis condition setting unit 0102, then the formula 0204 which is to be solved in this invention is obtained.

In here, m is the outward unit tangential vector perpendicular to its boundary line on the boundary of curvilinear surface. The formula 0204 is the second order elliptic equation with respect to the pseudo-displacement vector field d, and according to the stress estimation system of this invention, after obtaining the pseudo-displacement vector field d by solving the finite element discretized equation, stress field σ can be obtained by applying formula 0203. In this way, the stress analysis system of this invention is characterized as follows: By assuming that the mechanical equilibrium condition can be approximately expressed by the membrane stress field σ, and that the membrane stress field σ is represented by pseudo-displacement vector field d such as in formula 0203, the mechanical equilibrium equation 0201 concerned with membrane stress field σ can be converted into an equation with respect to pseudo-displacement vector field d such as in formula 0204.

Figure 3:
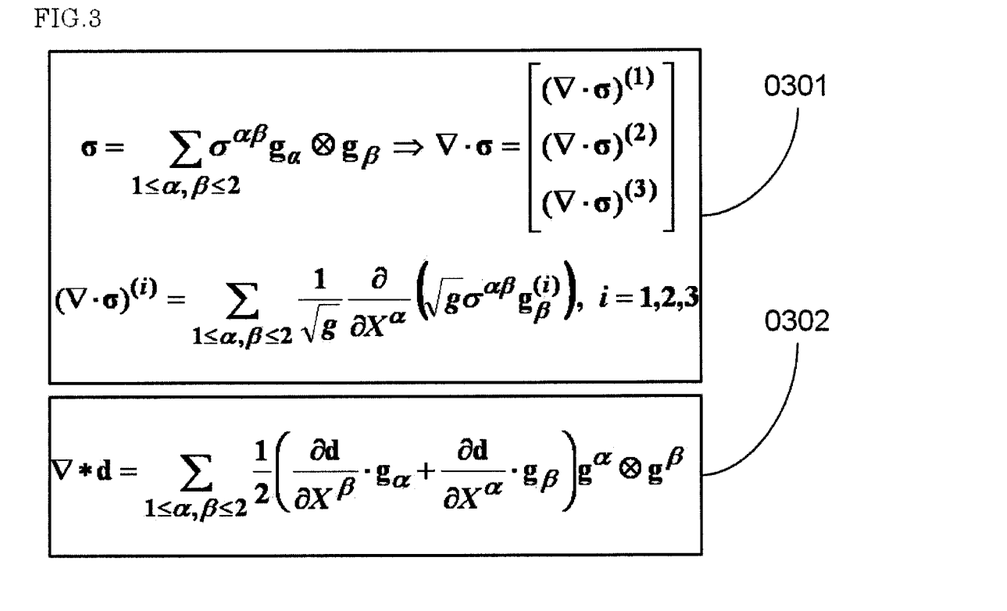
FIG. 3 A figure showing operator used in the theoretical explanation in FIG. 2.

FIG. 3 shows the operator used in the explanation of principle of this invention as depicted in FIG. 2. The formula 0301 defines vector field ∇·σ, the divergence of the membrane stress tensor field σ. The formula 0302 defines two-dimensional strain tensor field ∇*d using the pseudo-displacement vector d. In here, operator ∇· and −∇* are in adjoint relation with each other, and by this relation formula 0202 is derived from formula 0201 in FIG. 2.

Figure 4:
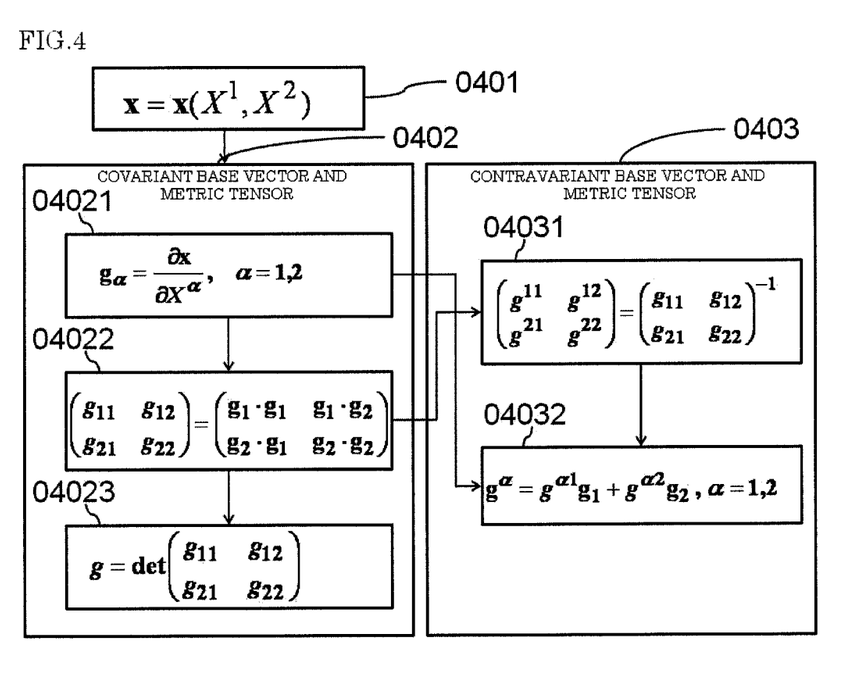
FIG. 4 A figure for explaining local coordinate system of the curvilinear surface, base vector and scalar amount of tangential plane concerned with local coordinate system used in FIG. 3.

FIG. 4 shows formula 0402 for obtaining covariant base vector and its metric tensor, formula 0403 for obtaining contravariant base vector and its metric tensor used in FIG. 3 from formula 0401 expressing curvilinear surface by local coordinate system $(X^1, X^2)$. However, formula 0401 indicating curvilinear surface expresses mapping $_x(X^1, X^2)$ from the local coordinate system $(X^1, X^2)$ to curvilinear surface. The formula 04021 is the formula for obtaining covariant base vector $g_1$, $g_2$ concerned with this local coordinate system, formula 04022 is the formula for obtaining metric tensor $(g_{\alpha \beta})$ and formula 04023 is the formula for obtaining its matrix g. The formula 4031 is the formula for obtaining metric tensor of contravariant base vector out of metric tensor of covariant base vector, and the formula 04032 is the formula for obtaining contravariant base vector $g^1$, $g^2$ corresponding to a given covariant base vector.

Figure 5:
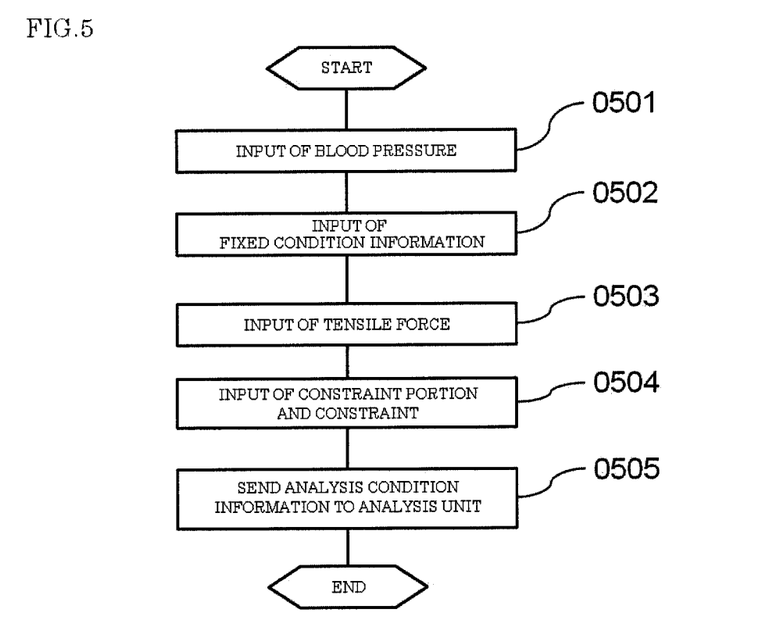
FIG. 5 A figure showing a flow of processing in interactive analysis condition setting unit in FIG. 1.
Figure 6:
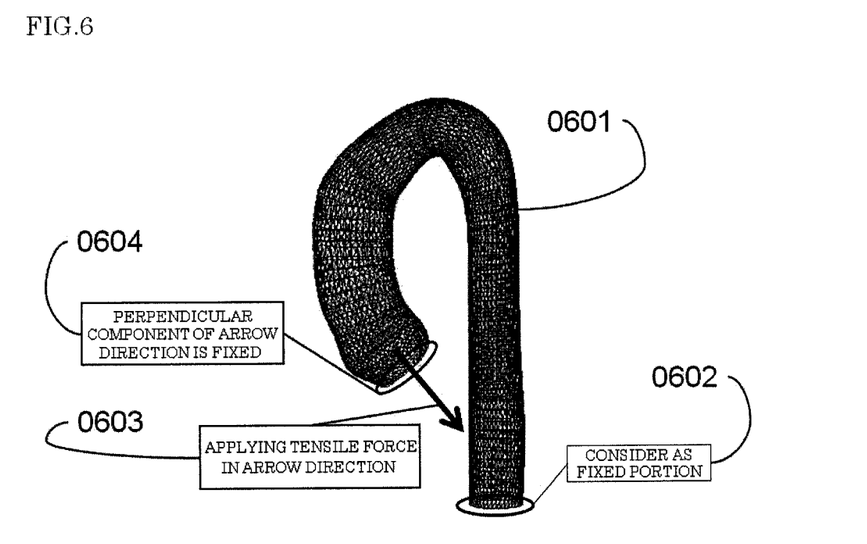
FIG. 6 A figure exemplifying a prescribed boundary condition in an example of vascular wall in aorta.

FIG. 5 is showing a flow of processing in an interactive analysis condition setting unit 0102. Furthermore, FIG. 6 shows boundary condition designating unit using vascular wall 0601 of aorta as an example. In 0501, vascular internal pressure p is inputted in reference with blood pressure measured externally. In 0502, fixed boundary condition (displacement of pseudo-displacement vector field d is set to zero) is designated as exemplified in 0602. In 0503, the boundary portion where tensile force is applied and the magnitude of tensile force are designated as exemplified in 0603. In 0504, on the boundary where the tensile force is applied as exemplified in 0604, the components of pseudo-displacement vector field d which are perpendicular to the direction of the force is set to zero.

Figure 7:
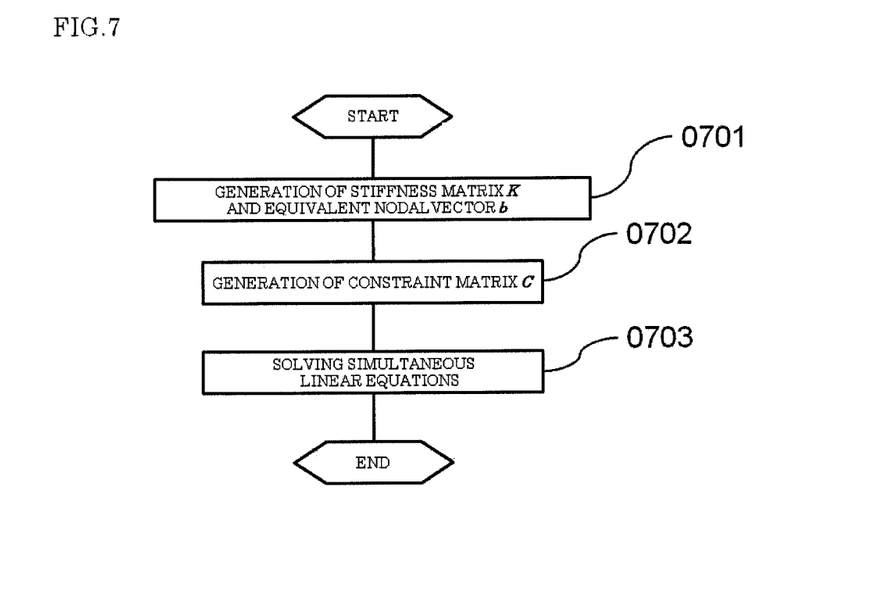
FIG. 7 A figure showing flow of processing in the calculation unit of pseudo-displacement vector field d in FIG. 1.

FIG. 7 shows a flow chart for showing a processing flow of calculation unit 0105 of the pseudo-displacement vector field d in FIG. 1. In 0701, stiffness matrix K and equivalent nodal force vector b are generated out of polygon data given by the polygon data input unit of curvilinear surface 0101, internal pressure p given by interactive analysis condition setting unit 0102 and tensile force f at curvilinear surface boundary, and constraint matrix c for expressing constraint given in 0702 is generated. Finally in 0703, with the stiffness matrix, equivalent nodal force vector and constraint matrix, a system of linear equations of the total system is constructed using Lagrange multiplier, and the pseudo-displacement vector field d is obtained by solving the simultaneous linear equations.

Figure 8:
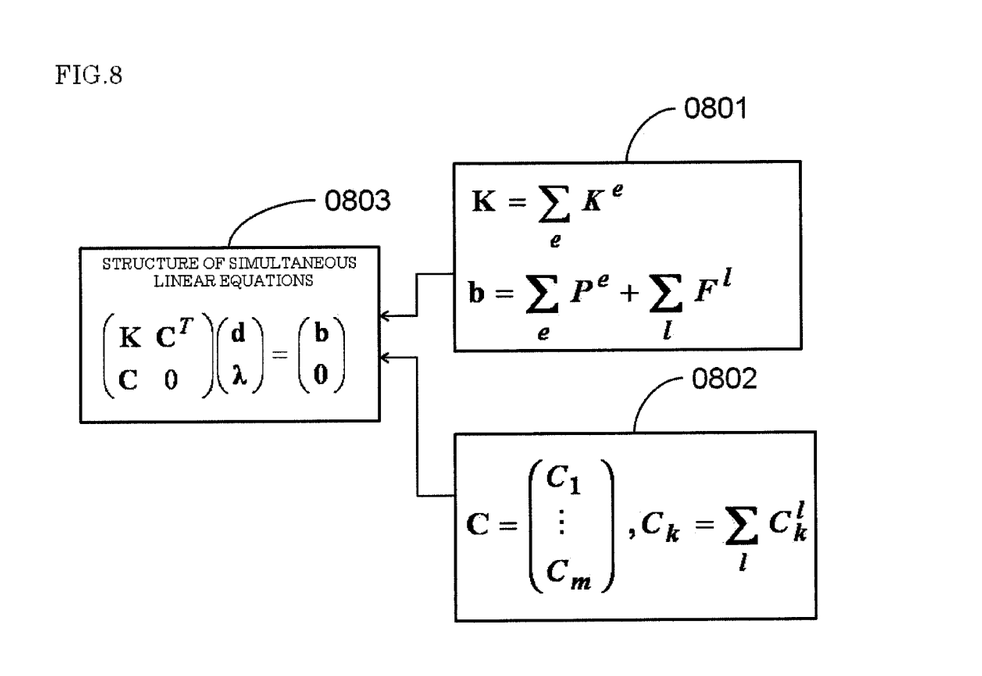
FIG. 8 A figure showing a configuration of simultaneous linear equation in FIG. 7.
Figure 9:
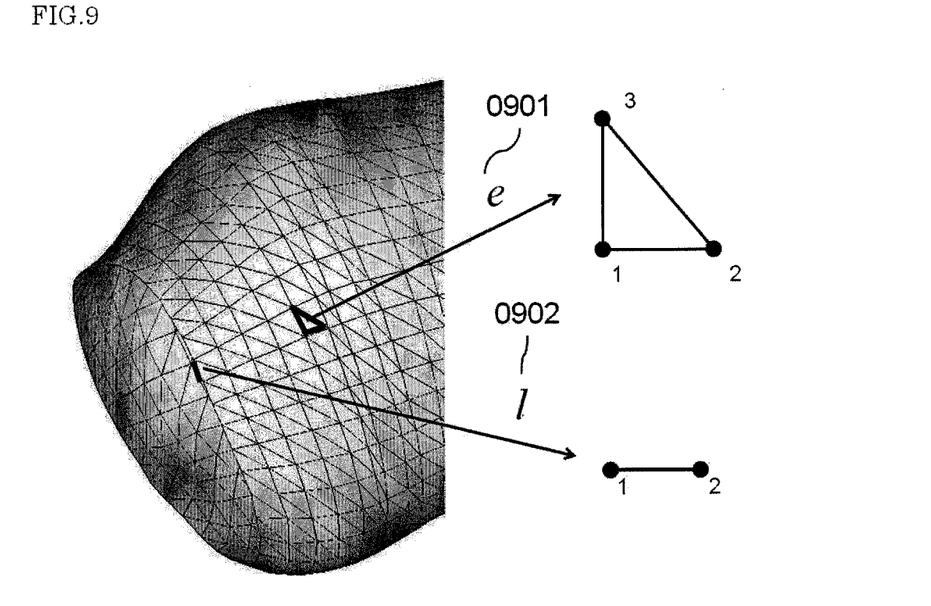
FIG. 9 A configuration diagram showing triangular element and boundary side.

FIG. 8 is showing structure of the simultaneous linear equation generated in FIG. 7. The stiffness matrix K and equivalent nodal force vector b generated in 0701 are constructed by superposing element stiffness matrices $K^e$, element equivalent nodal forces $P^e$ and equivalent nodal forces $F^l$ on element side which are concerned with each element e and side l at boundary as shown in 0801. In here, the element refers to polygon expressing curvilinear surface shape as shown in 0901 in FIG. 9, and the side at boundary refers to side of polygon positioned at curvilinear surface boundary.

In a similar manner, constraint matrix C generated in 0702 is structured by row vectors $C_k$ corresponding each constraint as shown in 0802, and the row vectors $C_k$ are generated by superposing matrix $C^l_k$ generated for the side at boundary. With the stiffness matrix K and equivalent nodal force vector b, simultaneous linear equation expressed in 0803 is obtained by applying the method of Lagrange multiplier for the constraint expressed by constraint formula Cd=0. In here, λ is the Lagrange multiplier vector.

Figure 10:
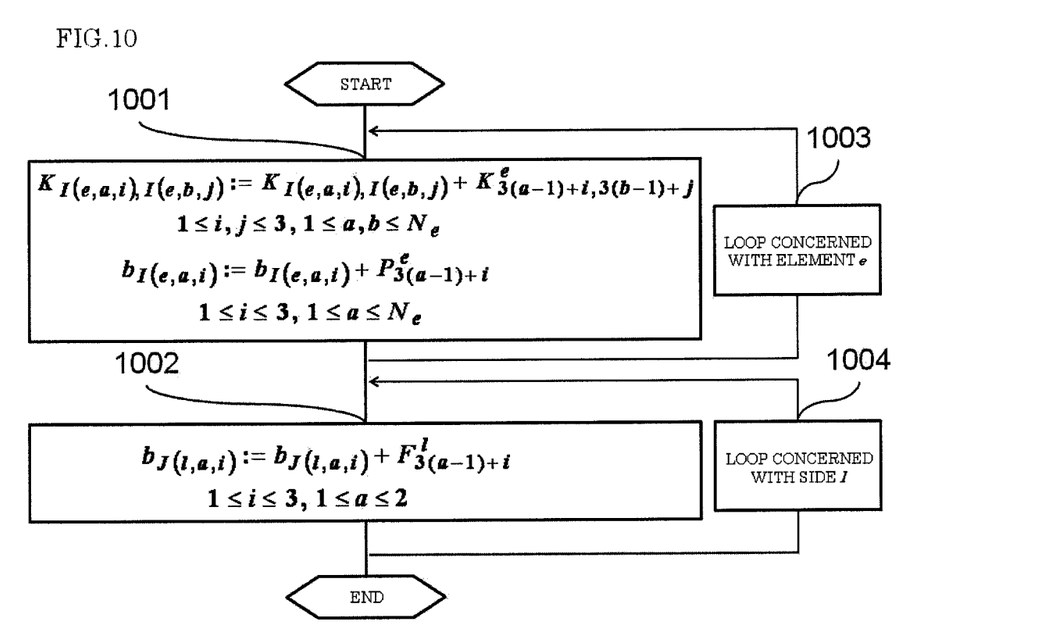
FIG. 10 A figure concretely showing a superposed calculation in 0801 of FIG. 8.

FIG. 10 is concretely showing overlapping calculation in 0801. In 1001, there is disclosed a method for superposing element stiffness matrices $K^e$ and element equivalent nodal forces $P^e$ for each element e. Ne is the number of nodes consisting the element, and the size of element stiffness matrices $K^e$ and element equivalent nodal forces $P^e$ is $3N_e$. I(e,a,i) is an index indicating where the i-th freedom of node a in element e is located in the global vector consisting of the total degree of freedoms. In accordance with this index, loop processing is carried out as shown in 1003, and the element stiffness matrices and element equivalent nodal forces of each element are superposed to K and b.

Figure 11:
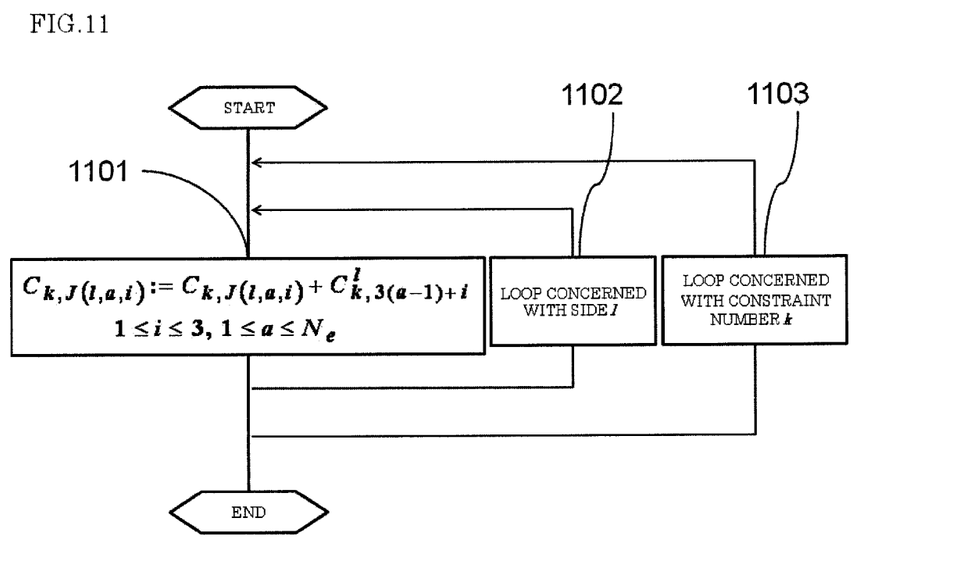
[FIG. 11] A figure for showing a method of generating a row vector in accordance with a constraint formula.

In a similar manner, 1002 indicates a method for superposing the side equivalent nodal forces $F^l$ defined by tensile force at each side l of boundary onto b. J(l,a,i) is an index indicating where the i-th freedom of node a at side l is located in the global vector consisting of the total degree of freedoms. Based on the index, loop processing concerned with l is carried out as indicted in 1004, side equivalent nodal forces are superposed onto b. Furthermore, 1101 in FIG. 11 indicates a method for generating row vector $C_k$ from k-th constraint formula in the same way as in 1002. In here, in the loop processing of 1103 concerned with constraint number k, loop processing 1102 concerned with side l is further carried out.

Figure 12:
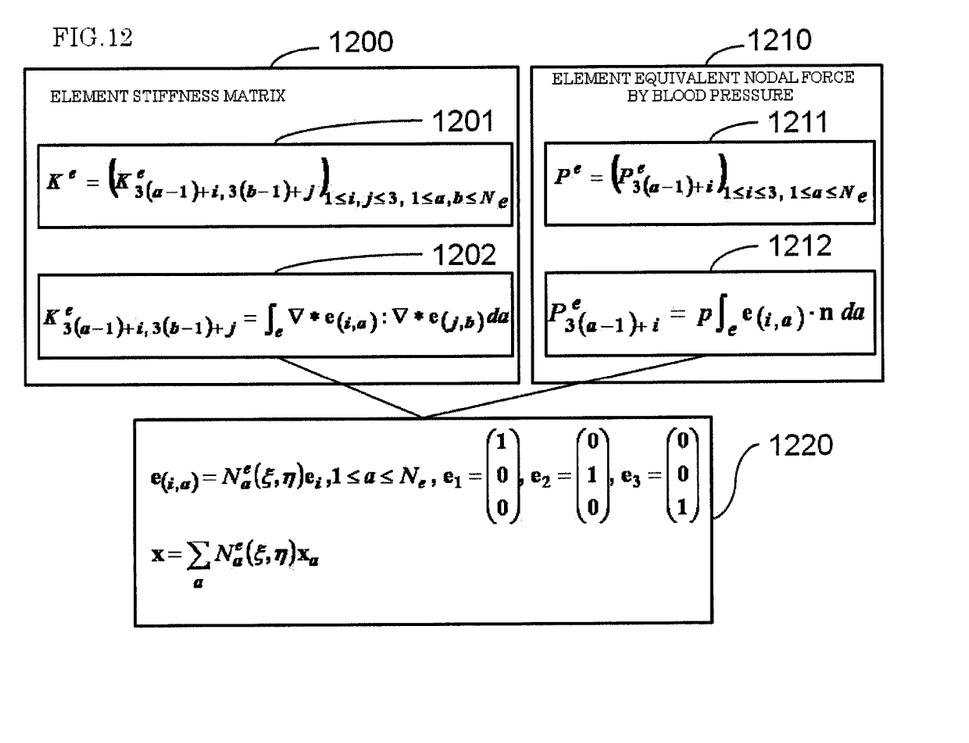
FIG. 12 A figure showing a calculation method of element stiffness matrix and finite element equivalent nodal force in each element.

In FIG. 12, 1200 indicates a calculation method of finite element stiffness matrix $K^e$ at each finite element and 1210 indicates a calculation method of finite element equivalent nodal force $P^e$ by blood pressure. And 1220 indicates how the pseudo-displacement vector field d and curvilinear surface shape x are interpolated from its nodal value at each finite element. Especially, $e_{(i,a)}$ is a vector value function while interpolating pseudo-displacement vector where the component corresponding to the i-th freedom of node a of the finite element is 1 and all the other degree of freedom are 0.

Also, $x_a$ is the coordinate at a-th node. 1202 shows calculation formula for each element of element stiffness matrix, where the operator defined in 0302 is applied to the vector value function defined by the above mentioned interpolation, and it is calculated by integrating on the surface defined by the interpolation. In here, finite element stiffness matrix $K^e$ is obtained by structuring the above obtained values as components as showing 1201. 1212 is also indicating calculation formula for each component of the element equivalent nodal force vector. In here, p is blood pressure given through 0501, and n is the unit outward normal vector (pointing a direction from intravascular to extravascular) of the curvilinear surface. By structuring vectors of which component values are obtained in above such as in 1211, element equivalent nodal force $P^e$ is obtained.

Figure 13:
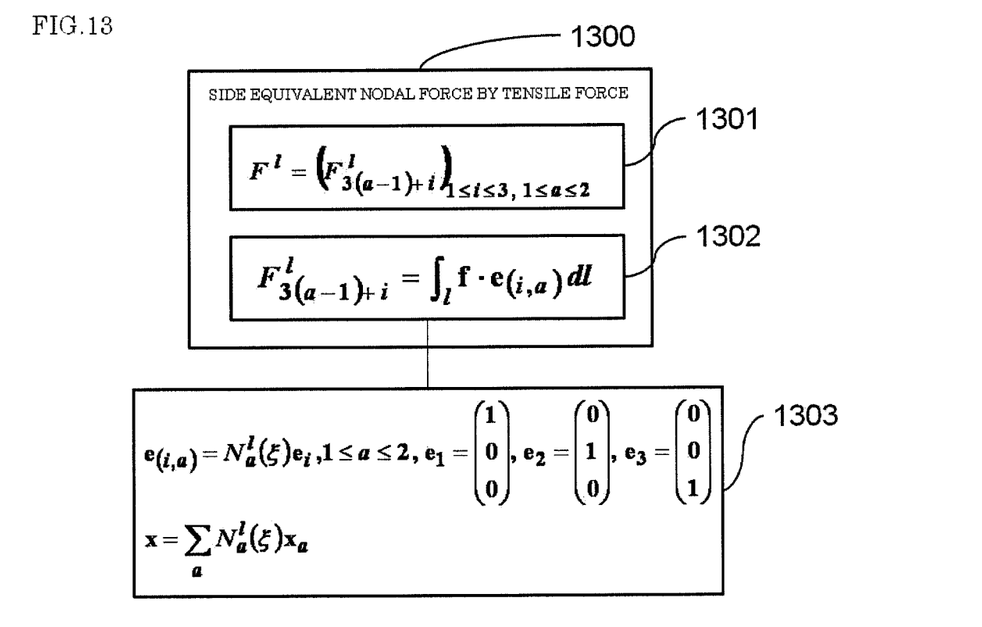
FIG. 13 A figure showing a calculation method of equivalent nodal force at each side of boundary.

In FIG. 13, 1300 indicates calculation method of side equivalent nodal force $F^l$ at each side of the boundary. 1303 indicates an interpolation method of pseudo-displacement vector field d and side shape on side l. 1302 is a calculation formula of each component of side equivalent nodal force $F^l$, where f is the tensile force given by 0503. And by structuring vectors of which the component values are obtained as shown in 1301, side equivalent nodal force $F^l$ is obtained.

Figure 14:
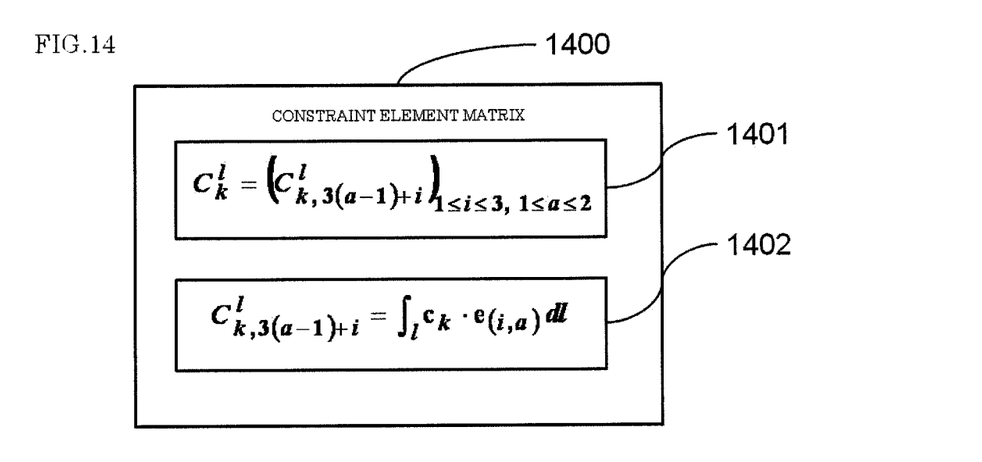
FIG. 14 A figure showing a calculation formula of constraint element matrix.

In FIG. 14, 1400 indicates calculation method for the component of contribution $C^l_k$ from side l while generating constraint row vector of k-th order. Vector $c_k$ in 1402 is generated by the information given at 0504, and constraint is given so as to make the inner product of vecto $c_k$ and the pseudo-displacement vector d zero. And by structuring vectors of which the components values are obtained as in 1401, the constraint row vector is obtained.

Figure 15:
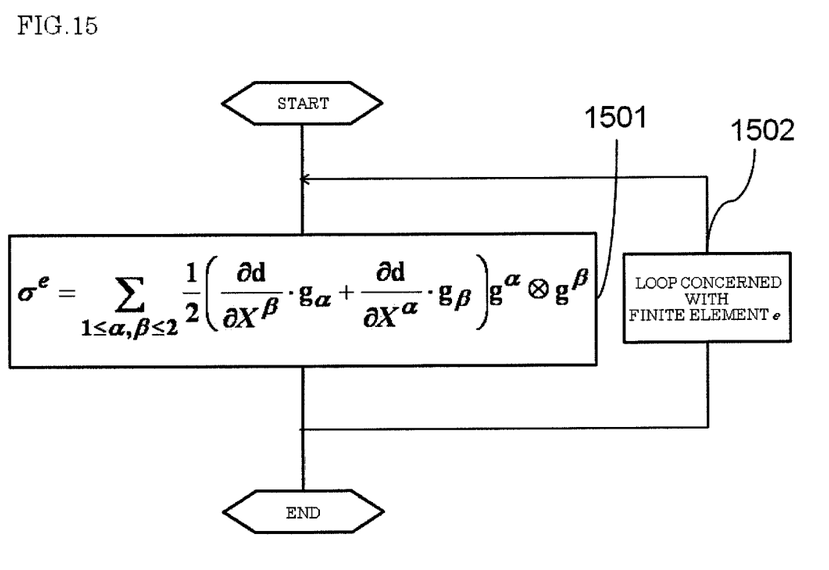
FIG. 15 A figure showing processing of membrane stress calculation unit 0106 in FIG. 1.

FIG. 15 shows a processing flow in the membrane stress calculation unit 0106. For the pseudo-displacement vector generated in a calculation unit 0105 of pseudo-displacement vector field d, membrane stress tensor $\sigma^e$ at each finite element e is generated as shown in 1501 based on 0203. However, for calculation in 1501, the interpolation equation which is identical with the equation shown in 1205 for curvilinear surface shape and displacement field is applied. In here, loop processing as to finite element e is carried out as shown in 1502, and membrane stress tensors on the entire finite elements are obtained.

Figure 16:
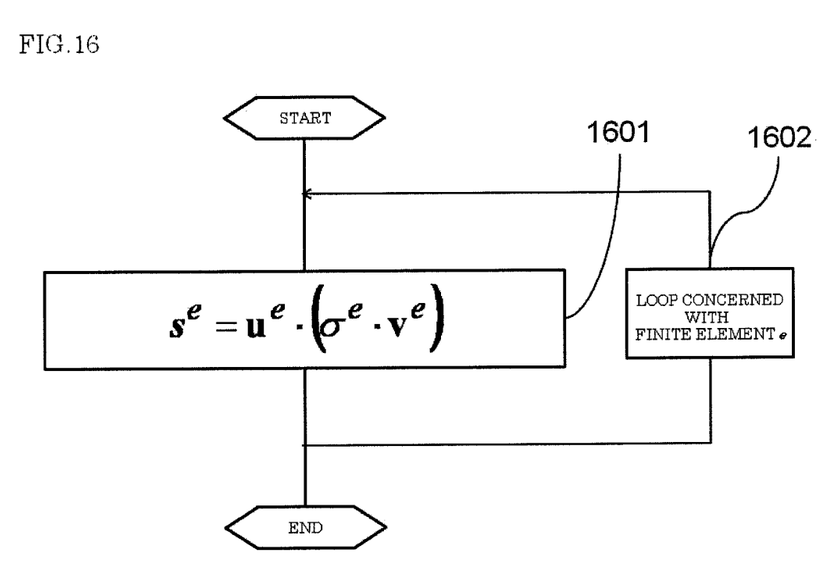
FIG. 16 A figure showing a processing of display stress calculation unit 0107 in FIG. 1.

FIG. 16 shows a processing flow in the display stress component calculation unit 0107. Base vector of designated component at each element is generated by the designation of stress displaying method given by the interactive visualization unit 0104, and the designated component is calculated for the membrane tensor given by the membrane stress calculation unit 0106 at each element. In here, loop processing for element e is carried out as shown in 1602, and the components of membrane tensor on entire elements are obtained. And the obtained data is passed onto the stress distribution visualization unit in interactive visualization unit 01014. And the stress distribution visualization unit displays such as a chart of stress distribution on the curvilinear surface or the maximum point of stress value to the user.

EXPERIMENTAL EXAMPLE 1

Figure 17:
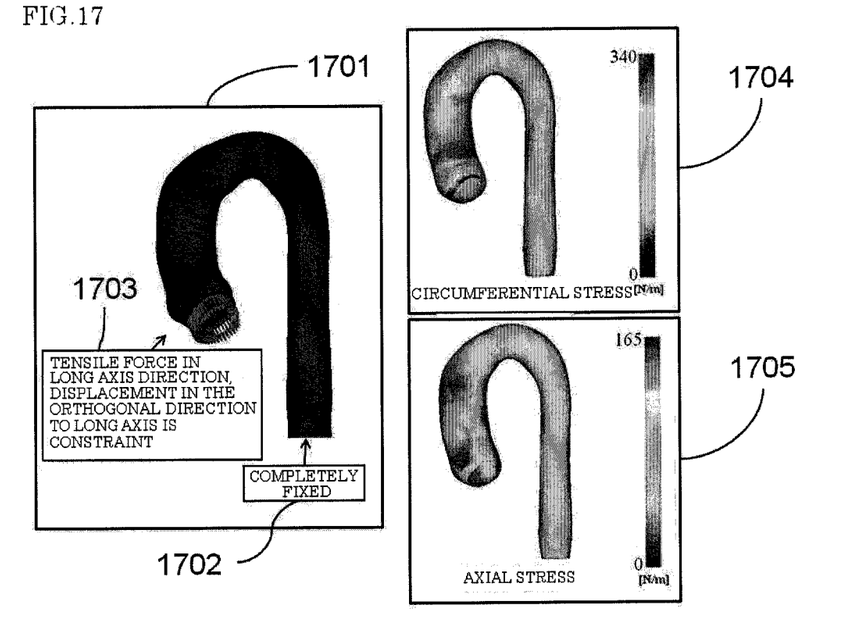
FIG. 17 A figure showing normal aorta polygon data and estimated stress in the experimental example 1.

In FIG. 17, a first experiment is shown. 1701 is a shape data of aorta vascular wall obtained from multi slice CT. Analysis condition as shown in 1701 is inputted through the interactive analysis condition setting unit 0102. In this practice, blood pressure of 120 mmHg is inputted in the blood pressure input unit 0501, lower end of descending aorta is set as being fixed in the fixed information input unit 0502 as shown in 1702, a uniform axial tensile force of which the total is equal to the product of blood pressure and sectional area of aorta root is set in the traction force input unit 0503 as shown in 1703, and constraint for the components of pseudo-displacement vector perpendicular to axial direction of root is designated at constraint unit and constraint input unit 0504.

Under the foregoing analysis condition, for the stress tensor calculated in stress analysis unit 0103, at interactive visualization unit 0104, circumferential and axial vectors are inputted, and 1704 displays the circumferential stress component, and 1705 displays the axial stress component. As shown by these stress distribution, in the stress estimating system of this invention, even an asymmetrical stress distribution can be easily estimated. Although, actually activating stress is not clear, it is confirmed that the stress obtained by structural analysis of three-dimensional finite element vascular model well coincides with the result of calculated stress by the stress estimating system of this invention.

EXPERIMENTAL EXAMPLE 2

Figure 18:
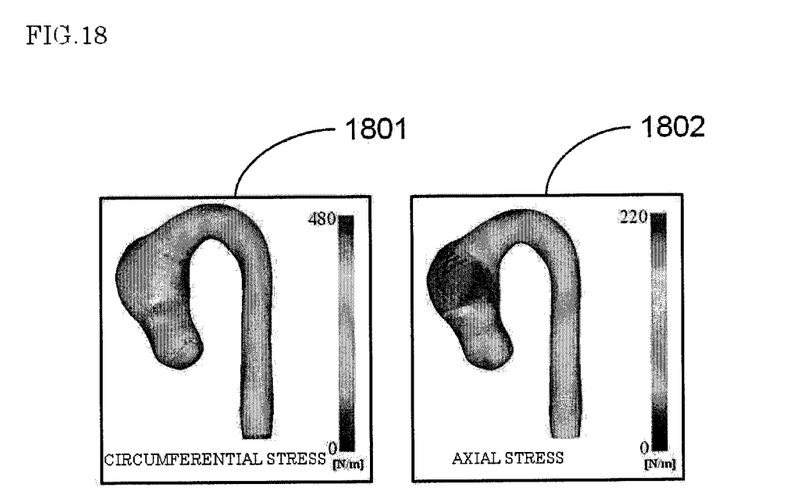
FIG. 18 A figure showing estimated stress where aneurysm of aorta exists in the experimental example 2.

In FIG. 18, there is disclosed a case where an aneurysm exists in ascending aorta, and obtained result of stress estimation carried out by applying a similar analytic condition as in the experimental example 1 through interactive analysis condition setting unit 0102. In interactive visualization unit 0104, vectors for circumferential and axial direction are inputted, and 1801 shows circumferential stress component and 1802 shows axial stress component, respectively. In the stress analysis system of this invention, stress estimation, even in a case where vascular shape is largely out of axisymmetry due to the existence of aneurysm, can be carried out without problems.

EXPERIMENTAL EXAMPLE 3

Figure 19:
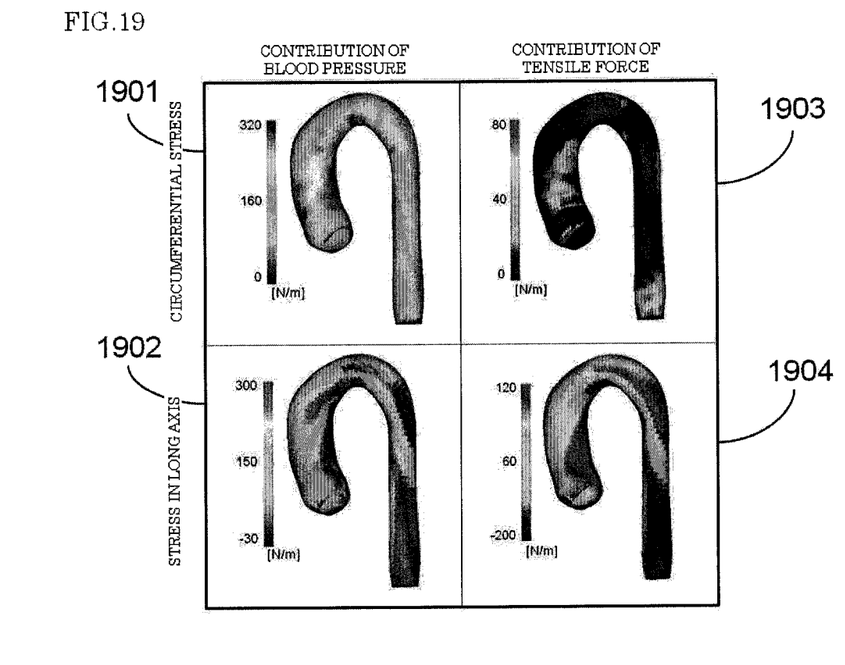
FIG. 19 A figure analyzing by separating effects from blood pressure and tensile force in the experimental example 3.

In FIG. 19, there is disclosed a result of stress estimation carried out by separating the effects of blood pressure and tensile force. In the beginning, blood pressure is set as 120 mmHg and tensile force is set as 0 in the interactive analysis condition setting unit 0102, then stress calculation is carried out at stress analysis unit under the same analysis condition as in the experimental example 1, circumferential and axial vectors are inputted in the interactive visualization unit 0104, and 1901 indicates circumferential stress component and 1902 indicates axial stress component.

Next, blood pressure is set to 0 and tensile force is set to the same as in the experimental example 1 in the interactive analysis condition setting unit 0102, then stress calculation is carried out in stress analysis unit under the same analysis condition as in the experimental example 1, circumferential and axial vectors are inputted in the interactive visualization unit 0104, and 1903 shows circumferential stress component and 1904 shows axial stress component. From this experimental example, it becomes detailed how each factor affects the stress distribution, for example as to circumferential stress component as seen from 1901 and 1903, contribution of blood pressure is dominant, and as to tensile force at aortic root, as seen in 1904 axial stress component is propagating spirally.

Figure 20:
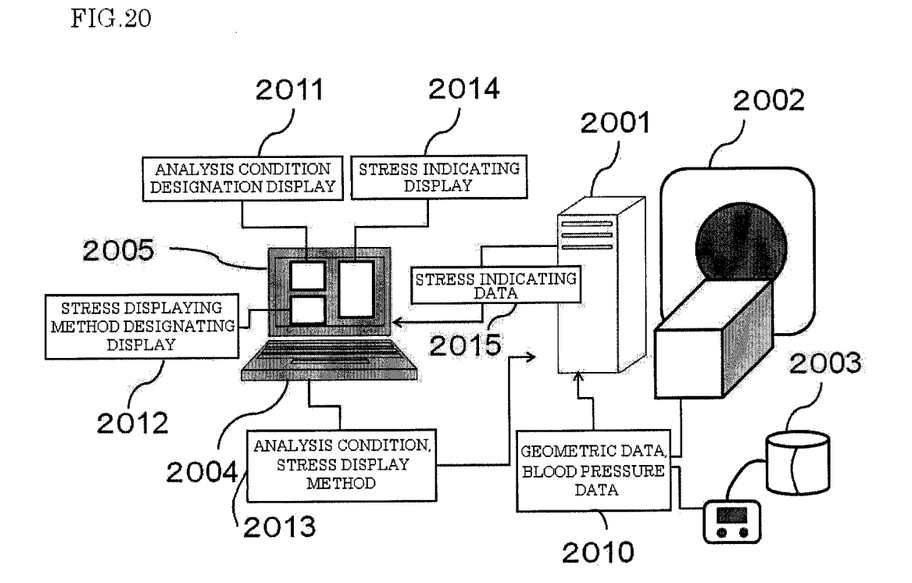
FIG. 20 A figure of a computer system for carrying out membrane stress estimation.

For realizing this invention, as shown in FIG. 20, in a computer system, shape and blood pressure data 2010 obtained by a diagnosis apparatus 2002 such as MRI, CT and ultrasound echo and a sphygmomanometer 2003, analysis condition and stress displaying method data 2013 are inputted into a computer 2001 by a keyboard 2004. In here, analysis condition and stress display method designated by a keyboard 2004 are displayed at an analysis condition designating display 2011 and stress display method designating display 2012 on a display 2005. These data are inputted into stress analysis unit as shown in FIG. 1 realized by internal program in computer 2001, and stress analysis is carried out. A stress display data 2015 generated in accordance with display method designated by calculated stress data is sent to the display 2005, and analysis result is displayed as shown in FIGS. 17, 18 and 19 in display 2014, and a clear diagnosis becomes possible.

Figure 21:
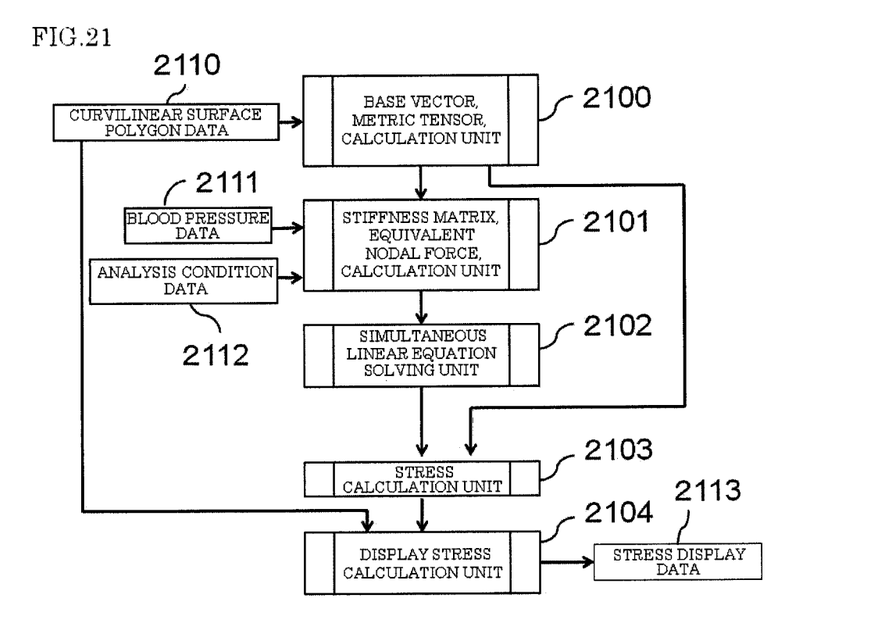
FIG. 21 A system figure of a membrane stress estimating unit composed of a logical calculation unit.

Also, each calculation processing as shown in FIG. 1 is not limited to the program realized on a computer, but also it is realized by a system composed by logical calculation unit as shown in FIG. 21. Base vector metric tensor calculation unit 2100 generates base vector and metric tensor as shown in FIG. 4 based on the input of curvilinear surface polygon data 2110 generated by the shape data. In stiffness matrix equivalent nodal force calculation unit 2101, from the base vector, metric tensor, blood pressure data 2111 and analysis condition data 2112, in accordance with FIGS. 10, 11, 12, 13 and 14, stiffness matrix equivalent nodal force are generated. In a solving unit of simultaneous linear equations 2102, from the data generated by the above mentioned stiffness matrix equivalent nodal force calculation unit 2101, simultaneous linear equations are generated in accordance with FIG. 8, and pseudo-displacement vector field is solved. In the stress calculation unit 2103, as shown in FIG. 15, inputting pseudo-displacement vector field data generated in the simultaneous linear equation solving unit 2102 and basic data generated in the base vector metric tensor calculation unit 2100, the stress tensor is generated. In the end, in the display stress calculation unit 2104, display stress component is generated out of stress tensor generated in the stress calculation unit 2103 as shown in FIG. 16, and stress display data 2113 is outputted together with curvilinear surface polygon data 2110. These are the data displayed in the stress displaying display.

In the above, although embodiments of this invention are practically explained, this invention is not limited to those embodiments, but it can be modified in various ways within the scope of this invention.

INDUSTRIAL APPLICABILITY

This invention, as a medical diagnosis system, can be utilized for such as diagnosis technology in order to evaluate the risk of rupture of vascular wall, from the current configuration of vascular wall surrounding blood domain obtained from medical image by diagnosis apparatus such as MRI, CT and ultrasound echo, and estimating stress distribution applied to the wall.

REFERENCE SIGNS LIST 0101 polygon data of curvilinear surface input unit
0102 interactive analysis condition setting unit
0103 stress analysis unit
0104 interactive visualization unit
0105 pseudo-displacement vector d calculation unit
0106 membrane tensor field σ calculation unit
0107 display stress component calculation unit
0108 stress display method designation unit
0109 stress distribution visualization unit
0601 vascular wall of aorta
0602 fixed boundary condition of vascular wall of aorta designation unit
0603 direction of tensile force
0604 traction of vascular wall of aorta designation unit
0901 example of finite element e
0902 example of side l
1701 shape data of aortic vascular wall obtained by multi slice CT
1702 completely fixed boundary condition in experimental example 1
1703 tensile force designation unit in the experimental example 1
1704 display of circumferential stress component in the experimental example 1
1705 display of axial stress component in the experimental example 1
1801 display of circumferential stress component in the experimental example 2
1802 display of axial stress component in the experimental example 2
1901 display of circumferential stress while considering only contribution of blood pressure in the experimental example 3
1902 display of axial stress while considering only contribution of blood pressure in the experimental example 3
1903 display of circumferential stress while considering only contribution of tensile force in the experimental example 3
1904 display of axial stress while considering only contribution of tensile force in the experimental example 3
2001 computer for executing membrane stress estimation program
2002 diagnosis apparatus for obtaining shape data
2003 sphygmomanometer for obtaining blood pressure
2004 keyboard for designating analysis condition and stress display method
2005 display for displaying analysis condition and analysis result
2010 shape data and blood pressure data inputted into computer
2011 analysis condition designation display
2012 stress display method designation display
2013 data of analysis condition and stress display method inputted into computer
2014 stress displaying display indicating stress distribution chart of analysis result

The invention claimed is:

1. A system for estimating membrane stress on an arbitrarily-shaped curvilinear surface based on current configuration data, comprising:
   a computer processor coupled to a non-transitory storage memory;
   a polygon data input unit configured to set polygon data of a curvilinear surface modeling a vascular wall;
   an interactive analysis condition setting unit configured to permit interactive setting of a blood pressure, a tensile force acting on a boundary of the vascular wall, and a prescribed constraint of the curvilinear surface at the vascular wall boundary;
   a stress analysis unit configured to obtain, under control of the computer processor, a two-dimensional stress distribution over the entire curvilinear surface structured by the vascular wall by analyzing mechanical equilibrium in accordance with membrane stress on the curvilinear surface based on the polygon data of the curvilinear surface inputted from the polygon data input unit and the prescribed constraint of the curvilinear surface set in the interactive analysis condition setting unit; and an interactive visualization unit configured to display interactively a distribution of at least a stress component of the two-dimensional stress distribution obtained by the stress analysis unit;

wherein the stress analysis unit is further configured to obtain, under control of the computer processor, the two-dimensional stress distribution by:

utilizing an adjoint operator of the divergence operator acting on a membrane stress tensor field, representing the membrane stress tensor field as a two-dimensional strain based on a pseudo-displacement vector field, the two-dimensional strain being independent of material properties of the vascular wall;

replacing the membrane stress tensor field in a finite element discretized model for the pseudo-displacement vector field with the two-dimensional strain;

obtaining a solution of the pseudo-displacement vector field from the finite element discretized model under the prescribed constraint set by the interactive analysis condition setting unit on a mesh given by the polygon data;

calculating the two-dimensional strain from the solution of the pseudo-displacement vector field; and obtaining the two-dimensional stress distribution from the calculated two-dimensional strain in accordance with the representing, independently of the material properties of the vascular wall.

2. A system for estimating membrane stress on an arbitrarily-shaped curvilinear surface based on current configuration data, comprising:

a diagnosis apparatus configured to obtain geometric data indicating geometry of a certain vascular portion of a patient;

a blood pressure data obtaining apparatus configured to obtain blood pressure data indicating blood pressure of a patient;

a designating condition input unit configured to input a designating analysis condition of the geometric data of the prescribed vascular portion and blood pressure data, and a stress display method for displaying a result analyzed under the analysis condition;

a computer processor coupled to a non-transitory storage memory;

a stress analysis unit configured, under control of the computer processor, to input a designation of the geometric data, blood pressure data, analysis condition and stress display method and generate stress display data by analyzing the geometric data, blood pressure data in accordance with the analysis condition and stress display method; and a display unit configured to display stress display data from the stress analysis unit;

wherein the stress analysis unit comprises:

a base vector metric tensor calculation unit configured to input curvilinear surface polygon data modeling the vascular portion generated in accordance with the geometric data and generate base vector data and metric tensor data;

a stiffness matrix equivalent nodal force calculation unit configured to generate a stiffness matrix equivalent nodal force in accordance with the base vector data, metric tensor data, blood pressure data and the analysis condition, independently of material properties of the vascular portion;

a simultaneous linear equation solving unit configured to input the stiffness matrix and equivalent nodal force to generate pseudo-displacement vector field data as a solution;

a stress calculation unit configured to input the pseudo-displacement vector field data and the base vector data to generate stress tensor data independently of the material Properties of the vascular portion; and a display stress calculation unit configured to generate a display stress component from the stress tensor data and generate stress display data by superimposing with the polygon data.

* * * * *